United States Patent [19]
Johnson et al.

[11] Patent Number: 5,441,533
[45] Date of Patent: Aug. 15, 1995

[54] AUTOMATIC FLUID CIRCULATING SYSTEM AND METHOD

[75] Inventors: Glenn W. Johnson, Summit; Henry J. McVicker, Chatham, both of N.J.; E. P. Erez Pick, Bayside, N.Y.

[73] Assignee: Aircast, Inc., Summit, N.J.

[21] Appl. No.: 180,706

[22] Filed: Jan. 13, 1994

Related U.S. Application Data

[63] Continuation of Ser. No. 968,287, Oct. 29, 1992, abandoned.

[51] Int. Cl.⁶ .............................................. A61F 7/00
[52] U.S. Cl. ................................... 607/104; 607/112; 601/13
[58] Field of Search ................. 128/400, 64, 402, 403, 128/379, 380, 40, 24.1; 165/46; 62/259.3, 570; 607/96, 104, 107, 108–114

[56] References Cited

U.S. PATENT DOCUMENTS

| | | |
|---|---|---|
| 1,732,380 | 10/1929 | Sarason . |
| 2,026,747 | 1/1936 | Nemzek . |
| 2,832,336 | 4/1958 | Davis et al. . |
| 3,403,673 | 10/1968 | MacLeod .............. 128/40 |
| 3,548,819 | 12/1970 | Davis et al. . |
| 3,633,567 | 1/1972 | Sarnoff . |
| 3,683,902 | 8/1972 | Artmenko .............. 607/104 |
| 3,862,629 | 1/1975 | Rotta .................... 128/64 |
| 3,901,225 | 8/1975 | Sconce . |
| 3,942,518 | 3/1976 | Tenteris ................. 128/64 |
| 4,139,004 | 2/1979 | Gonzalez, Jr. . |
| 4,149,529 | 4/1979 | Copeland et al. ........ 128/400 |
| 4,197,837 | 4/1980 | Tringali et al. ......... 128/40 |
| 4,335,726 | 6/1982 | Kolstedt ............... 128/400 |
| 4,338,944 | 7/1982 | Arkans . |
| 4,407,276 | 10/1983 | Bledsoe . |
| 4,628,932 | 12/1986 | Tampa . |
| 4,688,572 | 8/1987 | Hubbard et al. . |
| 4,872,448 | 10/1989 | Johnson, Jr. . |
| 4,951,665 | 8/1990 | Schneider . |
| 4,962,761 | 10/1990 | Golden ................. 128/400 |
| 4,964,402 | 10/1990 | Grim et al. . |
| 5,074,285 | 12/1991 | Wright ................ 128/24.1 |
| 5,080,089 | 1/1992 | Mason et al. . |
| 5,172,689 | 12/1992 | Wright ................. 128/400 |

OTHER PUBLICATIONS

Aircast Cryo-Cuff TM (various flyers showing the device).

M. B. Stringer et al.: Bone Joint Surg [BR] 1989; 71-B: 492-7—Deep Vein Thrombosis After Elective Knee Surgery.

Husni E., Ximines J., Hamilton F: Pressure Bandaging of the Lower Extremity, Use and Abuse. JAMA 206:2715–2718, 1968.

Duffley H, Knight K: Ankle Compression Variability Using the Elastic Wrap, Elastic Wrap with a Horseshoe, Edema II Boot, and Air-Stirrup Brace, Athletic Training 24:320–323, 1989.

Mindrebo N, Shelbourne D: Knee Pressure Dressings and their Effects on Lower Extremity Venous Capacitance and Venous Outflow, Methodist Sports Medicine Center, Indianapolis, Ind. 1989 (unpublished).

Effect of the Cryo/Cuff TM Knee Compression Dressing and an Elastic Wrap on Swelling of the Calf.

J. P. Sloan et al.: vol. 16, No. 8, Aug. 1988, *The Physician and Sportsmedicine*—"Effects of Cold Compression on Edema".

B. T. Cohn et al.: 0363-5465/89/1703-0344, vol. 17, No. 3 —*The American Journal of Sports Medicine*—"The Effects of Cold Therapy in the Postoperative Management of Pain in Patients Undergoing Anterior Cruciate Ligament Reconstruction".

(List continued on next page.)

Primary Examiner—Mark S. Graham

[57] ABSTRACT

A system and method for exchanging fluid between a body compress and a fluid source. In the preferred embodiment, an air pump is used to compress the fluid in the container and force it into the compress. When the motor is turned off, the fluid flows back from the container to the compress. By cycling the motor between "on" and "off" conditions, a circulation of fluid occurs between the compress and the container.

10 Claims, 5 Drawing Sheets

OTHER PUBLICATIONS

Letter dated Jun. 5, 1990, from Methodist Sports Medicine Center, regarding "Post-surgical Use of the Cryo-Cuff TM Knee Compression Dressing".

Committee on Complications of Arthroscopy Assn. of North America: *Arthroscopy: The Journal of Arthroscopic and Relating Surgery*, vol. I, No. 4, 214–200 (1985)—"Complications of Arthroscopy and Arthroscopic Surgery: Results of a National Survey".

Aircast Incorporated bulletin relating to the Aircast Cryo-Cuff TM—a prior art device of the instant assignee.

*Podiatric Products*, Jul. 1990, p. 14, "3K Cryotherapy Compression Bandage".

Advertisement of PI Medical, copyright 1990, "$CP_2$ Therapy Cold and Pressure Cold Pad".

"Interview of Dr. Kenneth L. Knight," *Orthopedic and Sports Medicine News*, pp. 1–5, date unknown.

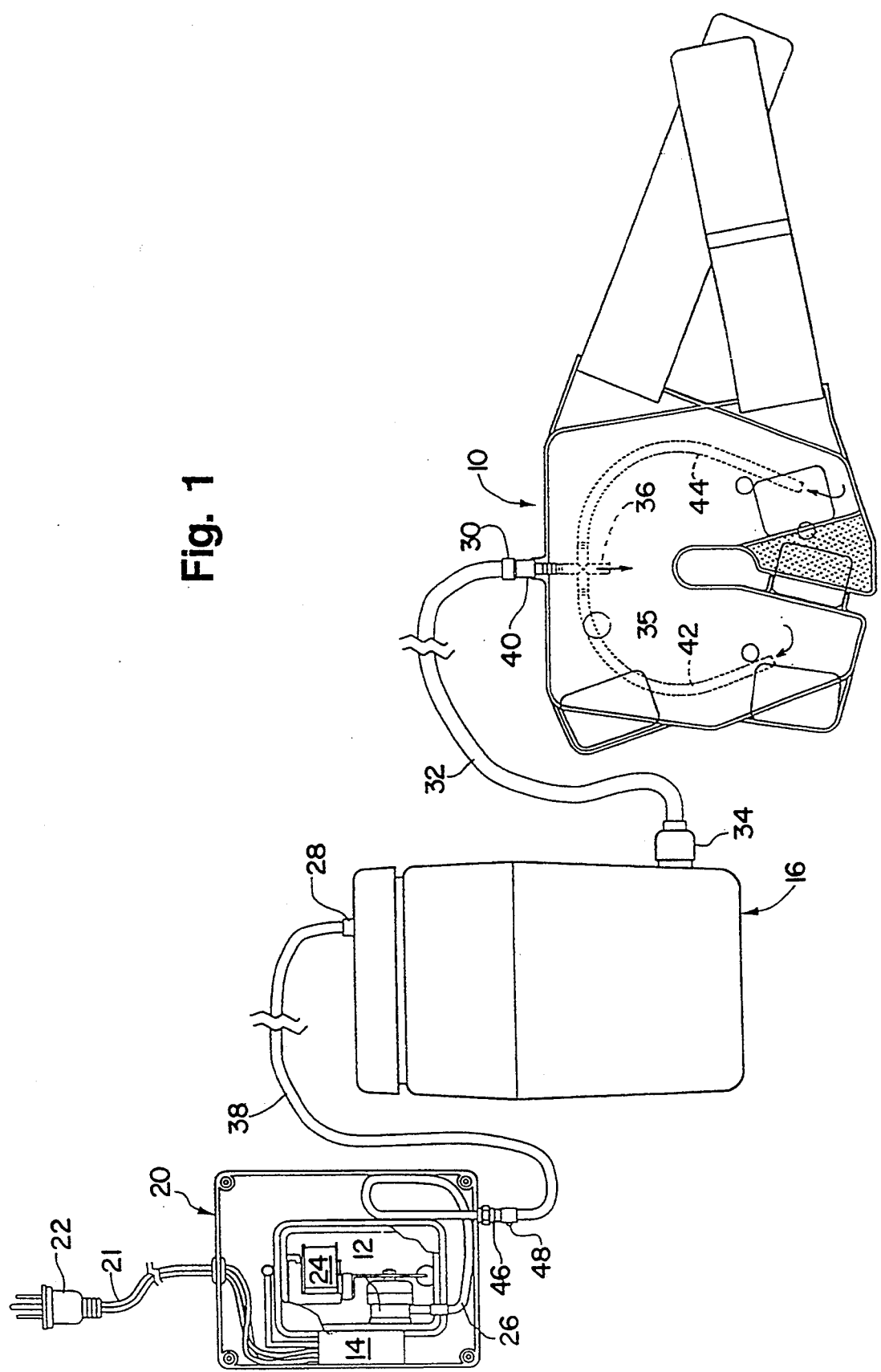

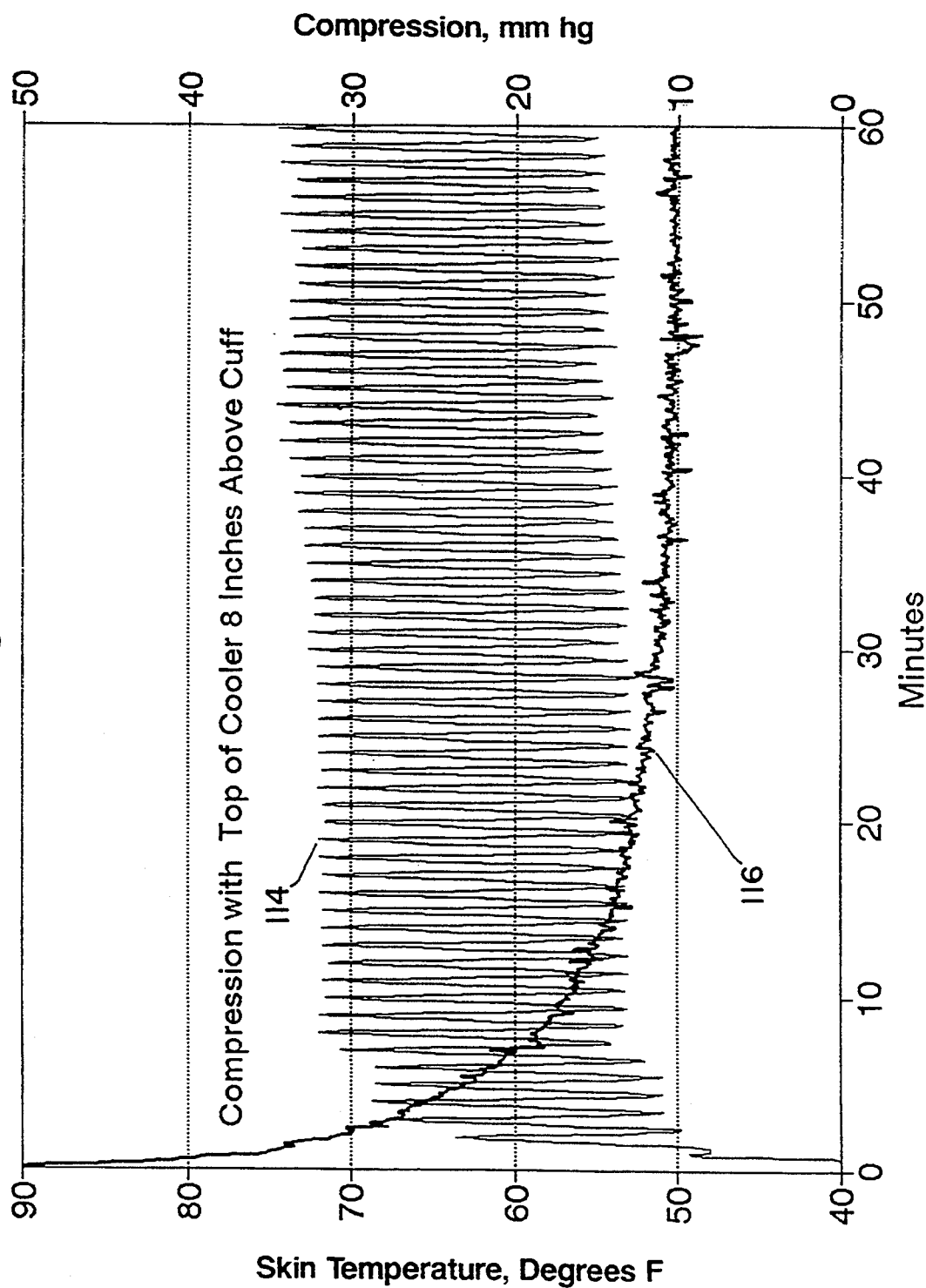

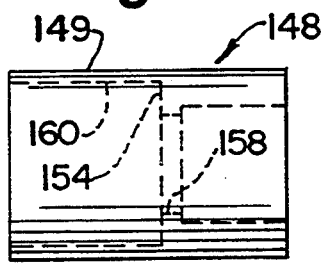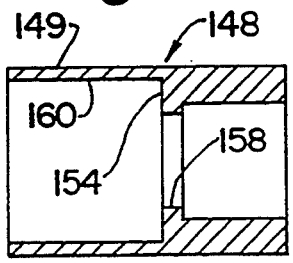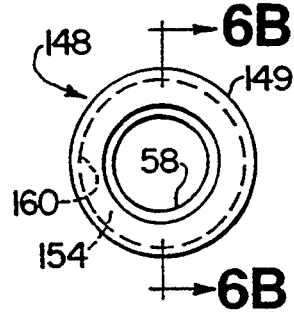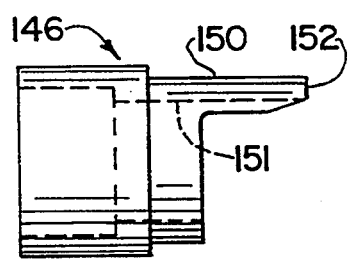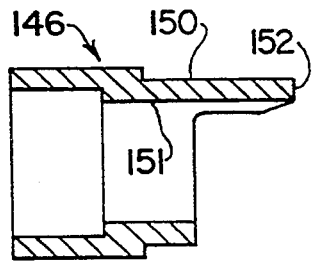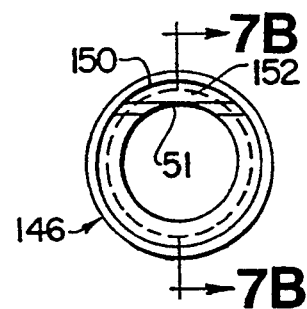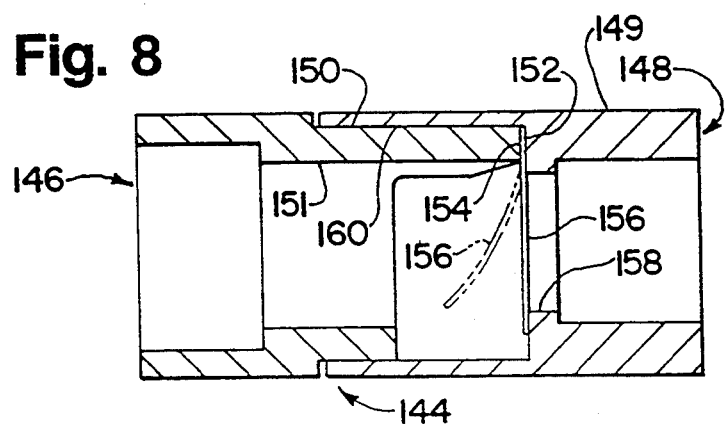

AUTOMATIC FLUID CIRCULATING SYSTEM AND METHOD

This is a continuation of application Ser. No. 07/968,287 filed on Oct. 29, 1992, abandoned.

FIELD OF THE INVENTION

The present invention relates to a simplified automatic apparatus and a method for treating bodily injuries and ailments and in particular to an improved pump system apparatus for circulating fluid between a fluid source of predetermined temperature and a hollow body compress to apply compression and a high or low temperature fluid to the affected area.

The invention specifically includes an improved air pump means for applying intermittent pneumatic compression to the fluid source to achieve automatic recycling of the fluid between the compress and source, so as to maintain contemporaneously temperature continuity in the compress/body interface and also to apply modest intermittent pressure changes to the affected area to increase the therapeutic effect.

BACKGROUND OF THE INVENTION

The therapeutic advantages of the application of intermittent compression to injured or afflicted areas of the body to prevent venous stasis and reduce the risk of emboli are well recognized by the medical profession today. However, the automatic systems available for such purposes tend to be bulky, expensive, and allow limited mobility of the patient during use. It also is well known that the application of cold and compression following injury or certain surgery is beneficial.

Present devices available for such purposes generally require manual pumping or movement of the chilled fluid from its source to recycle the fluid as it is warmed at the body interface. During such recycling, there is a concomitant deviation of pressure, thus, in effect, rendering the process less efficient than desired. Moreover, in certain instances, for example, when the compress device is applied to a shoulder, additional help is required to cycle the system. In addition, with these devices additional compression is sometimes applied with an elastic wrap over the cold device. In this event, the amount of compression is unknown, and may be excessive, and the applied compression is static rather than intermittent or pulsating as preferred.

In commonly assigned copending application Ser. No. 737,402, filed Jul. 29, 1991, U.S. Pat. No. 5,230,355 the therapeutic value of simultaneous application of cold and compression to an injured body part such as a knee is set forth. The invention disclosed therein, sold by the common assignee under the name "Aircast Cryo/Cuff," provides a simple and economical device that applies therapeutic cold and a first level of compression to the limited area of the knee that needs the therapy while using means for controlling the compression below the knee to a second predeterminable amount to minimize the constriction of venous circulation in the lower leg.

That invention includes a cuff-shaped compress with a watertight inflatable chamber shaped to envelope the anterior and sides of the knee including particularly the suprapatella pouch and the area of the knee just below the patella. Those are the areas where posttrauma body fluids accumulate and where cold and compression are most needed. The cuff is economically fabricated from sheets of flat material and its novel design permits adjustable shaping so as to conform to the knee even when the knee and cuff are flexed at different angles. The cuff is held in place with an upper proximal strap and a lower distal strap that avoid the popliteal area and minimize constriction. When the cuff is applied to the knee, the straps are secured but not tightened. A first amount of compression is then supplied to the knee by inflating the cuff to a reasonably predeterminable amount which causes the cuff chamber to expand. The expansion tensions the straps and applies compression to the areas of the knee under the chamber.

The cuff normally is strapped in place when empty and is then inflated with ice water which is supplied by a tube or fluid conduit from a cooler or container that is elevated above the cuff and the cuff is pressurized by gravity. With this technique, the amount of compression is determined by the elevation of the container above the cuff.

With such a device, chilled water becomes warm as it remains in contact with the body through the body/compress interface during treatment. Conversely, high temperature fluids are cooled as time passes. Thus, the effectiveness of both high and low temperature fluid treatments diminishes with time. Periodically, the fluid must be drained from the device and a fresh supply of fluid must be added.

The water from the cuff is routinely recycled back to the cooler for rechilling by lowering the cooler below the cuff. During the time required for rechilling the water, the pressure in the cuff falls and this permits even any minimal pooling of blood that might occur in the veins to be flushed out.

U.S. Pat. No. 5,080,089 attempted to remedy this problem of varying temperature at the cuff/body interface by providing an apparatus which, in one mode, allowed nonambient temperature fluid from a remote reservoir to be continuously circulated under pressure through a cuff wrapped around the injury. In another mode, air at ambient temperature is placed under pressure in the cuff and the cuff is sealed to apply compression, but not cold, to the limb. This has the advantage of near constant temperature without having to raise and lower the cooler periodically to recycle the water. However, the system is rather complicated and utilizes complex components, and is incapable of applying simultaneous compression and cold.

It is thus an object of the present invention to overcome the disadvantages of the prior art by providing a simple method of automatically and efficiently recirculating the fluid between the compress and the container to maintain general continuity of temperature at the compress/body interface, while simultaneously applying intermittent compression of a predetermined magnitude.

SUMMARY OF THE INVENTION

The instant invention relates to a system for the circulation of chilled or other fluids through a fluid conduit between a fluid container and a hollow body compress, the system comprising a connector in the container, a motor driven air pump coupled to the connector in the container and a timer coupled to the air pump motor to cause the air pump to cycle "on" and "off" for predetermined periods of time, and a means to depressurize the container, such that during the "on" cycle the container is pressurized and fluid is forced from the container into the compress and during the "off" cycle fluid is allowed to flow back to the container from the compress.

In a preferred embodiment of the present system, the compress is first applied to the injured body part and then filled with chilled fluid, and the container is placed at a desired level generally slightly higher than the compress to put the compress under pressure. Intermittent pneumatic pressure is then automatically applied to the fluid, preferably by utilizing a simple and inexpensive air pump coupled to the fluid container to pressurize the container in a cyclical fashion at predetermined intervals. A timer is coupled to the air pump to operate the motor in the desired intervals. Typically, the air pump is on for 30 seconds and then off for 30 seconds.

During the "on" cycle the increased air pressure in the container forces a few ounces of chilled water from the container to the compress. During the "off" cycle the air pressure is allowed to return to normal and a few ounces of warmed water returns from the compress to the container.

To relieve the air pressure during the "off" cycle a conventional solenoid operated air valve can be used. But this requires the cost and complexity of an extra component in the electrical circuit.

A surprisingly simple and effective alternative is to provide a continuous controlled air bleed in the system, where the bleed is large enough to permit relief of the pressure during the "off" cycle, yet small enough to permit the desired level of pressurization during the "on" cycle. It has been found that a bleed orifice in the range of about 0.020 to 0.025" will meet these requirements when used with a small economical vibratory air pump of the type commonly used to aerate aquariums, such as a pump having a flow rate of about 1000-1500 cc/min and an output air pressure of about 0.1-0.35 kg/cm$^2$. A more powerful pump would of course require the use of a larger orifice. A variable size bleed orifice can also be used. The orifice may be installed at the pump unit.

The cyclical flux of pressure, and flow of fluid to and from the compress also causes oscillating compression between the compress and limb. The amount of compression is a function of the elevation of the container in relation to the compress. For example, with the pump as described above operating on a one gallon container about 12" high, and with the top of the container level with the top of the compress, the compress/leg pressure oscillates between about 5 to 15 mm Hg. When the top of the container is about 8" above the compress, the pressure oscillates between about 15 to 35 mm Hg.

Because the fluid flows back and forth from container to compress, only a single connecting fluid conduit is required, instead of the dual tubes used in conventional recirculating systems. The conduit is preferably covered with an insulating sleeve to maintain the low temperature of the fluid.

When this system is used with ice water as the circulating fluid, the skin temperature under the compress falls rapidly to the 50° F. range. If this is too cold, the temperature can be regulated by turning a flow valve provided between the container and the compress. The cold is maintained as long as the ice in the container lasts, typically up to about eight hours with a gallon container of ice water.

BRIEF DESCRIPTION OF THE DRAWINGS

These and other objects of the invention will be more fully disclosed in conjunction with the following detailed description when taken in conjunction with the drawings in which like numerals represent like elements and in which:

FIG. 1 is a diagrammatic representation of the preferred embodiment of the present invention in which a motorized air pump is driven cyclically by a timer to pressurize the fluid container to force fluid through the fluid conduit to the compress during the "on" cycle and to allow the fluid to return through the conduit to the container during the "off" cycle;

FIG. 3 is a graph illustrating the skin temperature and compression achieved with the automatic circulation of chilled water with the present invention;

FIGS. 6A, 6B and 6C are a side view, cross-sectional view, and end view, respectively, of a first half of a novel check valve used in the present invention;

FIGS. 7A, 7B and 7C are a side view, cross-sectional view, and end view, respectively, of the second half of a novel check valve used in the present invention; and FIG. 8 is a cross-sectional view of the assembled novel check valve used in the present invention.

DETAILED DESCRIPTION OF THE DRAWINGS

Figure 2A:
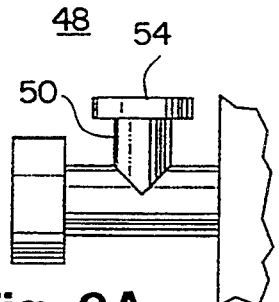
FIG. 2A is a side elevational view of the fluid conduit connector to the pump unit illustrating an orifice comprising an alternate bleed valve that is adjustable.

Although the description hereafter will refer to chilled water as being the fluid transferred from the fluid container to the compress, it is to be understood that a warm fluid could also be transferred from the container to the compress and thus the terms "chilled water" and "warmed water" would be interchangeable herein insofar as the operation of the device is concerned. Further, while the invention is disclosed as being applied to a knee cuff type of compress, it could also be used with a compress for the ankle, leg, arm, shoulder or other part of the body.

FIG. 1 is a diagrammatic representation of a preferred embodiment of the present invention. In FIG. 1, the fluid container 16 is coupled to the compress 10 with fluid conduit 32 and connectors 34 and 40. Pressure cuff or compress 10 is commercially available from the common assignee and is disclosed in detail in commonly assigned patent application Ser. No. 737,402, filed Jul. 29, 1991, entitled "Thermal Compress System" and incorporated herein by reference in its entirety. A small air pump unit 20 includes an air pump 12, an electrical timer 14 and a motor 24 in a common housing that can be plugged into a wall socket by means of plug-in type terminal 22. Air pump 12 is a standard vibratory air pump such as are used in aquariums and may be manufactured by EIKO ELECTRIC in Taiwan. The timer 14 is a timer of a type well known in the art such as those manufactured by CONTROL PRODUCTS CORP. in Grafton, Wis. It is a solid-state timer that may be arranged to have a desired duty cycle. A preferred duty cycle useful with the instant invention is 30 seconds on and 30 seconds off. Thus the motor 24 is turned on for 30 seconds and pump 12 pumps air through air hose 26 within air pump 20 to connector 46 having bleed valve 48 and through external air hose 38 to connector 28 of fluid container 16. As motor 24 runs for 30 seconds, it causes pump 12 to pressurize container 16, thus forcing a pre-determined volume of the chilled fluid through connector 34, conduit 32, and connector 40 to check valve 36 in the interior of compress 10. A fluid flow control valve 30 in connector 40 may be used to control the amount of fluid flowing from fluid conduit 32 into compress 10 to prevent overcooling by restricting fluid flow into compress 10.

The increased flow of water into compress 10 also increases the compression of the limb in contact with compress 10 during the "on" cycle, and the compression falls as the water returns to container 16 during the "off" cycle. When the top of container 16 is at about the same elevation as compress 10, the pressure oscillates between about 5 to 15 mm Hg above atmospheric pressure. When the top of container 16 is about 8 inches above compress 10, the pressure oscillates between about 15 to 35 mm Hg above atmospheric pressure. Thus the system provides a continuous application of cold, as well as oscillating compression of a predictable and adjustable magnitude.

The system is also surprisingly simple, economical and safe. There are no moving parts other than the vibratory pump. The pump is preferably a conventional aquarium-type air pump. Motor 24 is very small and uses very little power. The electricity is isolated to air pump unit 20 having an electrical cord 21 that is connected to plug 22 which is plugged into a wall socket. The pump motor 24 and timer 14 typically draw only about 4 watts of power 50% of the time. All electrical components are isolated from the water filled container 16 and compress 10 by air tube 38 that connects air pump unit 20 to the fluid filled container 16. This contrasts with the prior art recirculating systems, such as that disclosed in U.S. Pat. No. 5,080,089, that use a submersible electric pump within the fluid filled container, and draw approximately 10 watts of power continuously.

Because the water flows back and forth between container 16 and compress 10, only a single connecting conduit 32 is required, with single connectors 34 and 40 to container 16 and compress 10, respectively. This contrasts with the prior art recirculating systems that require two conduits, one for supply and the other for return flow from the compress, such as that disclosed in U.S. Pat. No. 5,080,089. Within compress 10, the efficient exchange of cold water for warm water may be enhanced by a one way check valve 36 in conduit stub 35. Check valve 36 opens during the "on" cycle to permit pressurized water to flow from container 16 into the top of the compress 10, but closes during the "off" cycle and forces the return of warmer water to container 16 through the ends of extension tubes 42 and 44 which extend substantially to the bottom of compress 10. This is facilitated by the short length of conduit stub 35, by the preferred right angle connection of extension tubes 42 and 44 to conduit stub 35, and by the surface tension resistance to fluid flow in extension tubes 42 and 44. Thus, as shown by the arrows in FIG. 1, cold water enters the top of compress 10 through one-way check valve 36 and warmed water returns to container 16 from the bottom of compress 10 through the ends of tubes 42 and 44, through connector 40, conduit 32, and connector 34. This arrangement provides more uniform distribution of the cold water, and precludes accumulation of a pocket of warm water at the top of the compress 10. The oscillating pressurization of the fluid container 16 on a cyclical basis provides the necessary compression and decompression of the compress 10.

FIG. 8 is a cross-sectional view of a one-way check valve 144 suitable for use as valve 36 of the present invention. Check valve 144 includes two sleeves 146 and 148. First sleeve 146 of check valve 144 has a reduced outer diameter portion 150 with a partial arcuate projection 151 extending from one end thereof below a segment of the reduced diameter. Second sleeve 148 of check valve 144 has an annular valve seat 154 on the interior thereof for receiving preferably a flexible urethane disc 156 of thickness of approximately 0.006 inch. The disc 156 is used to close and open an orifice 158 in sleeve 148. Orifice 158 is slightly smaller in diameter than the inner diameter 160 of sleeve part 148.

The disc 156 rests on the annular valve seat 154 on the interior of the sleeve 148, such that when the disc is in its resting position on the annular valve seat 154, insertion of the first sleeve 146 enables the partial arcuate projection 151 at the end 152 thereof to engage only an arcuate portion of one side of the flexible disc 156, so as to secure the disc 156 on only the one side between the first and second valve sleeve portions 146 and 148 in an interposed relation, thereby to block fluid flow in a direction from left to right in FIG. 8, but to allow fluid to flow in the opposite direction. The disc 156 is shown in the closed position by solid lines and in the open position in phantom lines. The sleeve 148 has an annular tube 149 that overlies the arcuate projection 151 and the extended portion 150 on sleeve 146.

FIG. 6A, FIG. 6B and FIG. 6C are a side view, cross-sectional view and end view, respectively, of the sleeve portion 148 of the check valve 144. As can be seen in FIG. 6A, the side view, the second sleeve 148 of check valve 144 has a body portion 149 that is cylindrical in shape externally. The cross-sectional view taken along lines 6B—6B of FIG. 6C is shown in FIG. 6B. The inside diameter 160 of body portion 149 is sufficient to receive in a press fit the first reduced diameter portion 150 of sleeve 146 as illustrated in FIG. 8. The second tube or sleeve 148 includes the annular valve seat 154 on the interior thereof for receiving the flexible circular disc 156 to block orifice 158. FIG. 6C is a side view of the portion 148 of check valve 144 shown in FIG. 6A.

The first sleeve 146 of the check valve 144 is illustrated in FIGS. 7A through 7C. FIG. 7A is a side view and illustrates the partial arcuate projection 151 extending from the outer reduced diameter end 150 of the first sleeve 146. The outside diameter is sufficient to be press fit into the inside of body portion 149 of the sleeve tube 148 as illustrated in FIG. 8. The arcuate projection 151 has a base end 152 that engages only an arcuate portion of one side of the flexible urethane disc 156, so as to secure the disc 156 on only one side between the first sleeve 146 and the second sleeve 148 in an interposed relation to block the orifice 158 when fluid flows in one direction, and to open the orifice 158 when fluid flows in the opposition direction.

Referring back to FIG. 1, connector 46 at pump unit 20 has a bleed valve 48 that bleeds the pressure to atmosphere constantly. This bleed valve 48 obviates the conventional solenoid-operated pressure relief valve, and also precludes any risk of excessive pressure buildup within the container 16. It has been found that in an apparatus of the instant invention using an air pump having a flow rate of about 1000–1500 cc/min and an output air pressure of about 0.1–0.35 kg/cm$^2$ and having a conduit 38 with an inner diameter of about 3/16" and an outer diameter of about ¼" a bleed valve orifice in the range of 0.020–0.025" in diameter, shown exaggerated in size in FIG. 4 at 48a and in greater detail in FIG. 2C, is large enough to bleed the pressure down during the "off" cycle yet small enough to permit adequate pressurization of container 16 during the "on" cycle.

Figure 2B:
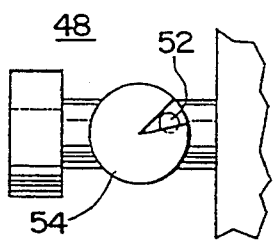
FIG. 2B is a top plan view of the bleed valve in the fluid conduit connector of FIG. 2A.
Figure 2C:
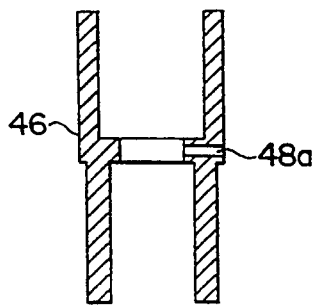
FIG. 2C is a cross-sectional view of the fluid conduit connector to the pump unit illustrating an alternate bleed valve having a non-adjustable orifice.

Alternatively, an adjustable bleed orifice may be a simple plastic molded part such as schematically and generally shown in FIGS. 2A and 2B. Bleed valve 48 includes a T connection 50 that has an orifice 52. By rotating plate 54, which has an arcuate section removed, the orifice 52 can be partially covered to any degree to regulate the amount of leakage. In one embodiment, if desired an adjustable bleed valve may be used that incorporates a timing disc from a timer disclosed in U.S. Pat. No. 2,981,533 incorporated herein by reference in its entirety. The timing disc has a groove that extends about 300° around the disc, one end of the groove communicates with the atmosphere and the other end with a pressure source. The amount of restriction is a function of the cross section of the groove and the length of travel of the air through the groove. Rotation of the disc provides linear adjustment. Thus, a rotation of 180° produces twice the restriction of at rotation of 90°.

FIG. 3 is a graph illustrating the skin temperature and compression with the automatic circulation obtained with the cyclically-operated motor system shown in FIG. 1, when a one gallon 12 inch high container 16 is elevated eight inches above compress ("cuff") 10.

Consider now waveform 114 which illustrates the 30-second cycle of time for the on/off operation of the motor 24 illustrated in FIG. 1. As can be seen in FIG. 3, the pressure graph or waveform 114 illustrates an example wherein during the "off" cycle the pressure drops to approximately 15 mm Hg and during the "on" cycle rises to approximately 35 mm Hg. The pressure oscillates between approximately 15 mm Hg and 35 mm Hg in a full one-minute cycle. It will be understood that these pressure values are approximate and will vary with the operating parameters of the system of the invention.

Note that the temperature curve 116 gradually decreases to approximately 50° and then maintains a substantially steady temperature. Thus, not only does the temperature hold substantially constant, but the pressure oscillates, which is beneficial as stated herein previously.

Figure 4:
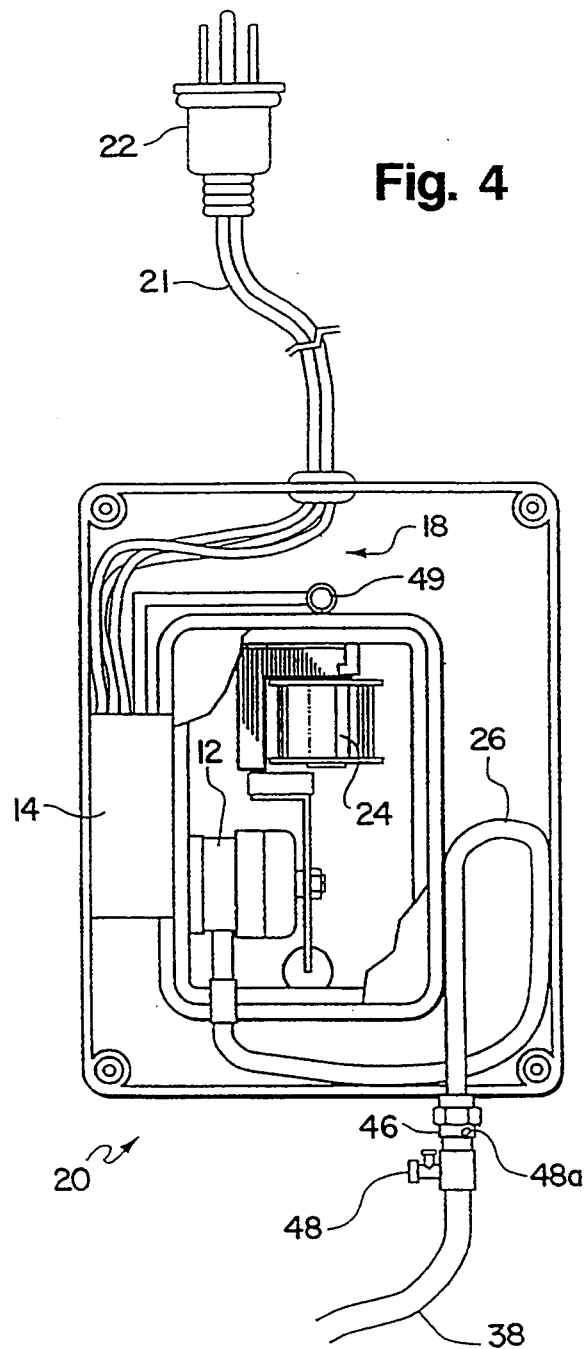
FIG. 4 is a front view of the pump unit with the cover removed to expose the internal components.

FIG. 4 is a view of the air pump unit 20 with the cover removed and shows the basic air pump motor 24 that may be of the type manufactured by EIKO ELECTRIC CO. Motor 24 drives an air pump 12 and, in combination, they form a standard aquarium-type vibratory pump unit. A solid-state timer 14 is made by CONTROL PRODUCTS CORPORATION in Grafton, Wis. The output of the air pump 12 through tube 26 is coupled to the connector 46 which is in communication with bleed orifice 48 (or 48a). Hose 38 couples the connector 46 to the connector 28 of the container 16 as shown in FIG. 1. Clearly, the bleed orifice 48 could be placed anywhere along air tube 38 from connector 46 on the pump unit 20 to the connector 28 on the container 16. In this invention, the preferred embodiment is as shown in FIG. 1. Power is supplied through cord 21 and plug 22 which may be plugged into a power receptacle. Indicator light 49 provides a visual indication that the device is receiving power.

In operation, reviewing FIG. 1, container 16 is filled with fluid at a desired temperature, such as ice water, and the compress 10 is applied to an injured body part such as the knee as in the manner for normal manual operation. The container 16 is positioned such that the top of it is about level with the top of the compress 10, for example by resting container 16 on a table or hanging it from a bedside rack. Container 16 has an air vent, not shown, which is closed. The pump unit 20 is plugged into an electrical wall socket with plug 22 and its air tube 38 is connected to the top of container 16 at connector 28. The pump unit 20 is designed for continuous operation and may consume only two watts of power. The timer 14 turns the pump motor 24 on for 30 seconds of each minute. The pump 12 increases the air pressure in the container 16 to a maximum of about 27 mm Hg and forces ice water from the container 16 into the compress 10. The compress 10 will fill in five or six minutes. Then, with each cycle, a few ounces of fresh ice water will flow into the compress 10 and warmed water will return from the compress to the container 16. This cyclic flow of water in and out of the compress 10 enables intermittent pneumatic compression of the compress and stabilizes the water temperature in the compress. The graph in FIG. 3 illustrates the skin temperature and compression as explained previously.

Figure 5:
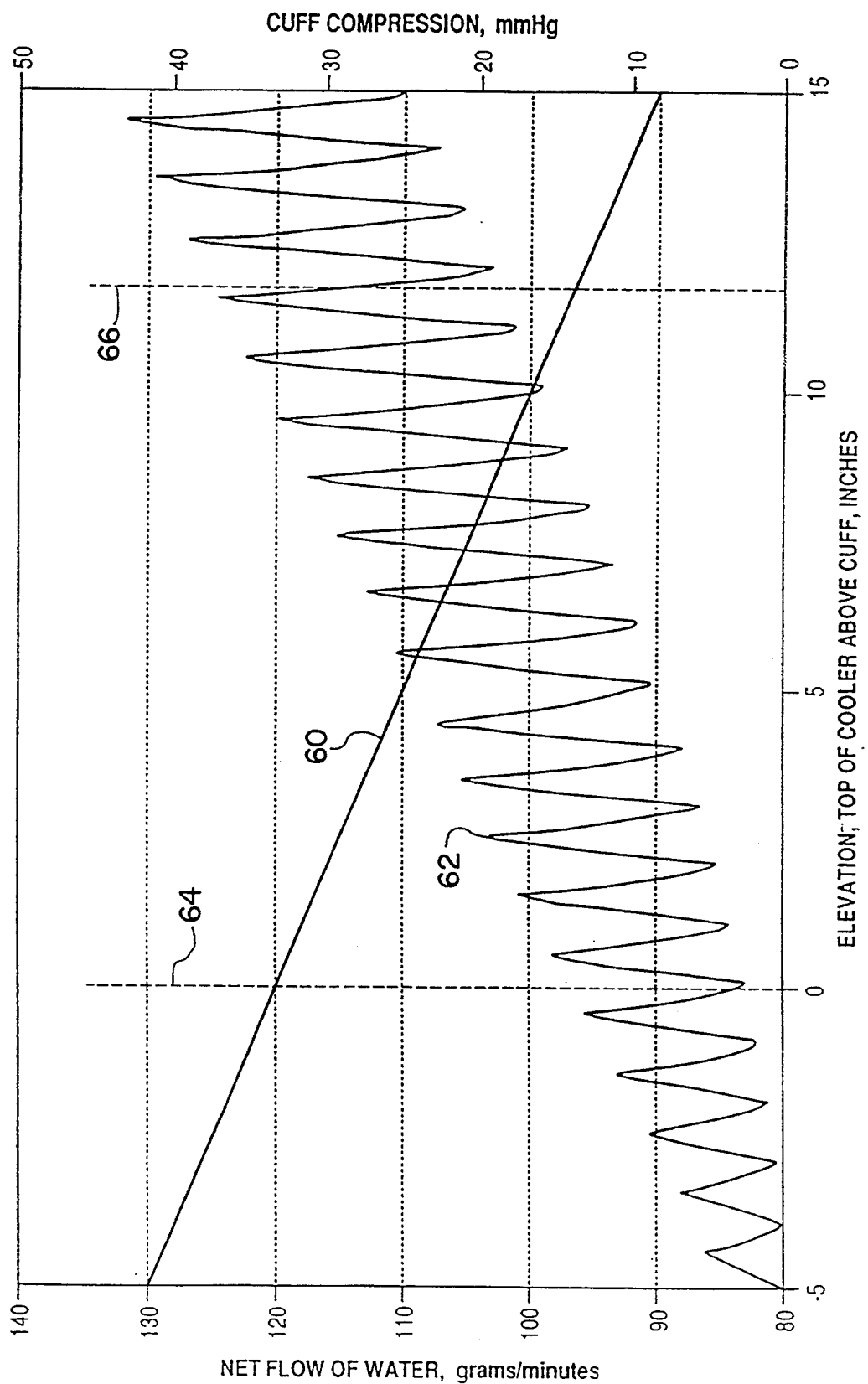
FIG. 5 is a graph illustrating the relationship of the elevation of the container with respect to the compress and the resulting net water flow to and compression of the compress.

Both the amount of water exchanged with each cycle and the change in compression with each oscillation are easily regulated by adjusting the elevation of the container 16 above the compress 10. A single bedside hook, not shown, facilitates this adjustment. The graph in FIG. 5 illustrates the relationship. Line 60 illustrates the net flow of water with respect to elevation of the container 16 while waveform 62 illustrates the change in pressure or compression with change of elevation of the container 16. The recommended elevation of the container 16 is shown to be between lines 64 and 66 representing a range of 0 to approximately 12 inches of the fluid in container 16 above the compress 10.

There has been disclosed a preferred embodiment of the present invention that includes a small motor, such as an aquarium-type air compressor motor that is driven cyclically by a timer. The motor is coupled to an inlet on the fluid container and, when the motor is operating, it compresses the fluid in the fluid container and forces the fluid into the compress. When the motor is off, fluid returns from the compress to the container to be recycled.

While the invention has been shown and described with respect to a particular embodiment thereof, this is for the purpose of illustration rather than limitation; other variations and modifications of the specific embodiment herein shown and described will be apparent to those skilled in the art all within the intended spirit and scope of the invention. Accordingly, the patent is not to be limited in scope and effect to the specific embodiment shown and described nor in any other way that is inconsistent with the extent to which the progress in the art has been advanced by the invention.

We claim:

1. A system for the automatic transfer of chilled fluid at a non-ambient temperature from a single fluid-holding container to a hollow body compress to be applied to a mammal, and back to said fluid-holding container to provide oscillating pressure to said hollow body compress, the system comprising:
- a fluid-holding container;
- a hollow body compress suitable for application to a mammal;
- a fluid conduit for providing two-way fluid communication directly between said container and said compress;
- a motor driven air pump operatively coupled with said container to provide pressurized air thereto;
- an automatic pressure relief means operatively coupled between said air pump and said container for continuously relieving the pressure; and
- means coupled to the air pump motor to cause the air pump to cycle "on" and "off" for predetermined periods of time; said pressure relief means having a capacity small enough such that during the "on" cycles said air pump is able to pressurize said container to force chilled fluid from said container into said compress and to increase the pressure in said compress, and said pressure relief means having a capacity large enough such that during the "off" cycle said container is at least partially depressurized through said pressure relief means so that fluid is allowed to flow back to the container from the compress through the fluid conduit to decrease the pressure in said compress, and to allow the fluid which flows back to the container to be rechilled, whereby said system provides oscillating pressure to said compress.

2. A system as in claim 1 further comprising:
- a fluid flow control device coupled to said fluid conduit at a first location within said compress; and
- at least one extension tube extended from said fluid conduit to a second location within the compress remote from said first location such that during the "on" cycle fluid forced into the compress enters said compress through said fluid flow control device at the first location and during the "off" cycle fluid leaves the compress through said extending tube from said second location to facilitate recirculation of the fluid between the container and the compress over a period of time.

3. The system of claim 2 wherein said fluid flow control device is a one-way check valve.

4. The system of claim 3 wherein said one-way check valve comprises:
- a first sleeve and a second sleeve, said first sleeve having an end with an outer diameter such that said end can be inserted in an end of the second sleeve in a fluid-tight relationship; and
- a flexible circular disc interposed and secured between the end of said first sleeve and the interior of said second sleeve so as to allow fluid flow in one direction but not the other, the diameter of the disc being slightly smaller than the inside diameter of said end of said first sleeve and slightly larger than the inside diameter of the second sleeve.

5. The system of claim 4 wherein said one-way check valve further comprises:
- an arcuate projection extending from the outer end of the first sleeve; and
- an annular valve seat on the interior of the second sleeve for receiving the flexible circular disc such that when said disc is resting on said annular valve seat, insertion of the end of said first sleeve into said second sleeve enables the arcuate projection to engage only an arcuate portion of one side of the flexible disc so as to secure the disc only on one side between said first and second sleeves in an interposed relationship to allow fluid flow in one direction and present fluid flow in the opposite direction.

6. The system of claim 1 wherein said air pump has a flow rate in the range of about 1000–1500 cc/min and an output air pressure in the range of about 0.1–0.35 kg/cm$^2$, and wherein said pressure relief means is a bleed orifice in the range of about 0.020–0.025 inches, and wherein during the "on" cycle the pressure in the compress is in the range of about 15–35 mm Hg.

7. A system for the circulation of fluid through a fluid conduit connected between a fluid container and a hollow body compress, the system comprising:
- a fluid container;
- a hollow body compress;
- a fluid conduit connected between said fluid container and said hollow body compress;
- a first fluid flow control means positioned at a first location in the compress and coupled to said fluid conduit for allowing fluid flow only into the compress from the container;
- at least one extension tube extending from said fluid conduit to a second location in the compress remote from the first fluid flow control means for allowing fluid to flow out of the compress; and
- pressurizing means coupled to the interior of the fluid container for cyclically pressurizing the container such that fluid is forced from the container through the connecting fluid conduit into the compress at said first location and fluid is forced from the compress back to the container only from the second location in the compress during the cyclical pressurization.

8. A method for providing oscillating pressure and a chilled fluid of substantially constant non-ambient temperature to a hollow body compress, comprising the steps of:
- providing a hollow body compress;
- providing a single container having therein a quantity of chilled fluid at a non-ambient temperature;
- providing a fluid conduit for two-way fluid communication directly between said container and said compress;
- coupling a motor-driven air pump to said container;
- providing a pressure relief means between said air pump and said container that is continuously open to atmosphere;
- coupling a timing circuit to said air pump to cause said air pump to cycle "on" and "off" for predetermined periods of time, said pressure relief means being of a capacity small enough such that during the "on" cycle said air pump is able to pressurize the container and force chilled fluid from the container through the fluid conduit into the compress to provide pressure and a chilled fluid of non-ambient temperature directly from said container to said compress, said pressure relief means being of a capacity large enough such that during the "off" cycle the container is at least partially depressurized through said pressure relief means to allow fluid to flow directly back to the container from the compress through the fluid conduit and thereby reduce the pressure of the compress and to allow the fluid which flows back to the container to be rechilled, whereby the fluid is recycled directly between the compress and the container to maintain a substantially constant non-ambient temperature of the fluid in the compress while the pressure in said compress oscillates.

9. A method as in claim 8 further comprising the steps of:
coupling a fluid flow control device to said fluid conduit within said compress to allow fluid to flow into said compress in only one direction; and
providing at least one extension tube from said fluid conduit to a location within said compress to a location remote from said control device, said control device allowing fluid to flow into the compress such that during the "on" cycle fluid is forced into the compress through the fluid flow control device and during the "off" cycle the fluid flows from the compress only at said remote location to assist in total circulation of the fluid between the container and the compress over a predetermined period of time.

10. The method of claim 9 further including the step of using a one-way check valve as the fluid flow control device.

* * * * *